(12) United States Patent
Bevinakatti et al.

(10) Patent No.: US 8,536,349 B2
(45) Date of Patent: Sep. 17, 2013

(54) CYCLIC ETHERS

(75) Inventors: Hanamanthsa Shankarsa Bevinakatti, Cleveland (GB); Christopher Paul Newman, Kent (GB); Simon Ellwood, Rüschlikon (CH); Pietro Tundo, Mestre (IT); Fabio Arico, Padua (IT); Martin Schroeder, Winterthur (CH)

(73) Assignee: Givaudan S.A., Vernier (CH)

( * ) Notice: Subject to any disclaimer, the term of this patent is extended or adjusted under 35 U.S.C. 154(b) by 552 days.

(21) Appl. No.: 12/669,003

(22) PCT Filed: Jul. 14, 2008

(86) PCT No.: PCT/GB2008/050567
§ 371 (c)(1),
(2), (4) Date: Jun. 16, 2010

(87) PCT Pub. No.: WO2009/010791
PCT Pub. Date: Jan. 22, 2009

(65) Prior Publication Data
US 2010/0274030 A1 Oct. 28, 2010

(30) Foreign Application Priority Data
Jul. 13, 2007 (GB) .................................. 0713598.1

(51) Int. Cl.
*C07D 309/00* (2006.01)

(52) U.S. Cl.
USPC ....................................................... 549/356

(58) Field of Classification Search
USPC ....................................................... 549/356
See application file for complete search history.

(56) References Cited

U.S. PATENT DOCUMENTS

| | | | |
|---|---|---|---|
| 3,029,255 A | 4/1962 | Stoll |
| 3,050,532 A | 8/1962 | Schumacher et al. |
| 4,203,908 A | 5/1980 | Mueller et al. |
| 4,866,188 A | 9/1989 | Scheben |
| 5,274,134 A | 12/1993 | Bruns et al. |
| 5,811,560 A | 9/1998 | Knuebel et al. |
| 6,380,404 B1 | 4/2002 | Davey et al. |
| 2005/0165229 A1 | 7/2005 | Best et al. |

FOREIGN PATENT DOCUMENTS

JP  02-167274  6/1990

OTHER PUBLICATIONS

Search Report for Great Britain Application No. GB0713598.1 (Nov. 14, 2007).
Muri et al., "Pseudo-peptides derived from isomannide as potential inhibitors of serine proteases," Amino Acids, vol. 28, pp. 413-419 (2005).
Zhao et al., "Palladium(II)-Catalyzed Enyne Coupling Reaction Initiated by Acetoxypalladation of Alkynes and Quenched by Protonolysis of the Carbon-Palladium Bond," J. Org. Chem., vol. 70, pp. 4059-4063 (2005).
Honda et al., "New approaches to the industrial synthese of HIV protease inhibitors," Org. Biomol. Chem., vol. 2, pp. 2061-2070 (2004).
Mereyala et al., "Simple Entry into Isonucleosides: Synthesis of 6-amino-9-[(3S,4S,5R)-4-hydroxy-5-(hydroxymethyl)tetrahydrofuran-3-yl]purine," Tetrahedron Letters, vol. 45, pp. 295-2966 (2004).
Qian et al., "Platinum-Catalyzed Intramolecular Hydroalkoxylation of γ- and δ-Hydroxy Olefins to Form Cyclic Ethers," J. Am. Chem. Soc, vol. 126, pp. 9536-9537 (2004).
Kulagowski et al., "Stereocontrolled Syntheses of Epimeric 3-Aryl-6-phenyl-1-oxa-7-azaspiro[4.5]decane NK-1 Receptor Antagonist Precursors," Organic Letters, vol. 3, No. 5, pp. 667-670 (2001).
Ho et al., "Alkylglycidic Acids: Potential New Hypoglycemic Agents," J. Med. Chem., vol. 29, pp. 2184-2190 (1986).
Pattison, "Cyclic Ethers Made by Pyrolysis of Carbonate Esters," J. Am. Chem. Soc, vol. 79, pp. 3455-3456 (Jul. 5, 1957).
International Search Report and Written Opinion of the International Searching Authority for International Application No. PCT/GB2008/050567 (Apr. 15, 2011).
Zawisza et al., "Palladium-Catalyzed Formation of Cyclic Ethers—Regio-, Stereo- and Enantioselectivity of the Reaction,"European Journal of Organic Chemistry, pp. 2296-2309 (2007).

*Primary Examiner* — Noble Jarrell
*Assistant Examiner* — Raymond Covington
(74) *Attorney, Agent, or Firm* — Jenkins, Wilson, Taylor & Hunt, P.A.

(57) ABSTRACT

A process of preparing cyclic ethers is described. The process involves the reaction of at least one organic compound such as a dioi or a polyol which it has at least one pair of hydroxyl groups separated by 4 or 5 carbon atoms, and which is capable of being converted into an ether linkage, with an organic carbonate in the presence of a base. The base is an alkoxy, a carbonate or a hydroxide base or is a mixture of such bases. At least one of the hydroxyl groups of the organic compound is not a tertiary hydroxyl group.

13 Claims, No Drawings

CYCLIC ETHERS

The present invention relates to cyclic ethers and, more particularly, to methods of making cyclic ethers.

Cyclic ethers in the form of anhydro sugar alcohols have many applications in food, therapeutic uses etc and are used as monomers for polymers and copolymers. Such anhydro sugar alcohols are, in particular, derivatives of mannitol, iditol, and sorbitol, the formula for sorbitol being:

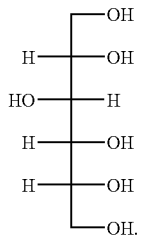

A particularly useful anhydro sugar alcohol derived from sorbitol is isosorbide, ie 1,4:3,6-dianhydrosorbitol, which has the formula:

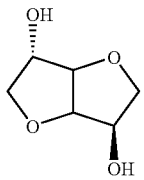

and which is useful as a monomer in the manufacture of polymers and copolymers, especially polyester polymers and copolymers. Isosorbide may also be converted into other useful compounds, for example dimethyl isosorbide, ie 1,4:3,6-dianhydrosorbitol-2,5-dimethyl ether. Dimethyl isosorbide may be considered a "green" solvent since sorbitol may be sourced from various natural resources and, consequently, may be regarded as a renewable natural resource. Isosorbide is used as a solvent in medical applications; as an ingredient in cosmetic formulations; and as a formulation medium.

Such anhydro sugar alcohols may be produced by the dehydration of the corresponding sugar alcohols (or mono-anhydro sugar alcohols). The dehydration is effected using dehydration catalysts, typically strong acid catalysts. Examples of such catalysts include mineral acids, such as sulphuric and hydrochloric acids, sulphonated polystyrenes, typically in the presence of solvents such as water or organic solvents such as toluene or xylene Other cyclic ethers, such as tetrahydrofuran, may also be made by dehydrating dials, for example.

Some cyclic ethers have distinctive aromas and are useful as fragrances. For example (−)-norlabdane oxide, the full chemical name of which is 1,2,3a,4,5,5a,6,7,8,9,9a,9b-dodecahydro-3a,6,6,9a-tetramethylnaphtho-(2,1-b)-furan and which has a structure:

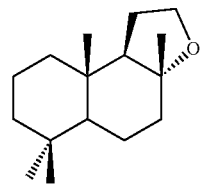

is a well known fragrance material, which is widely used for providing ambergris-type odours to perfumes. Ambergris is a metabolic product of blue sperm whales which has been used in the past as a valuable constituent of fine fragrances. Natural ambergris itself is no longer used for this purpose. However, there is a demand for perfume ingredients with ambergris-type odours. The compound (−)-norlabdane oxide represents one of the preferred synthetic compounds with desirable ambergris-type odour and is commercially available under various trade names (notably as Amberlyn, Ambroxan, Ambrofix, Ambrox or Amberoxide).

A number of synthetic procedures for norlabdane oxide have been published starting from the naturally occurring (−)-sclareol, which may be converted into 8α,12-dihydroxy-13,14,15,16-tetranorlabdane, which has the structure:

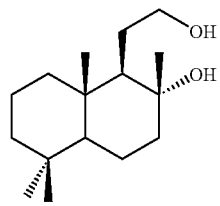

and which may be dehydrated to give (−)-norlabdane oxide.

Examples of such synthetic procedures include those described in U.S. Pat. No. 3,029,255, U.S. Pat. No. 3,050,532, U.S. Pat. No. 5,274,134, U.S. Pat. No. 5,811,560 and U.S. Pat. No. 6,380,404.

Other methods of making cyclic ethers may include oxidation of alkenes with peroxyacid such as m-CPBA (mostly used for epoxide synthesis); intramolecular nucleophilic displacement of alkyl halides by alkoxides (ie intramolecular nucleophilic substitution of a halohydrin); and addition of an alcohol to a double bond and ether formation by tosylation and subsequent tosyl displacement. More recent methodologies also include: Platinum Catalysed Hydroalkoxylation of γ- and δ-hydroxy olefins (H. Qian, X. Han, R. A. Widenhoefer, *J. Am. Chem. Soc.*, 2004, 126, 9536-9537); Palladium-catalysed Inter- and Intramolecular Enyne Coupling Reaction (L. Zhao, X. Lu, W. Xu, *J. Org. Chem.*, 2005, 70, 4059-4063).

It has also been proposed to make cyclic ethers by the pyrolysis of the corresponding carbonate ester of selected triols, see for example Dexter B Pattinson, Cyclic Ethers Made by Pyrolysis of Carbonate Esters, J. Am. Chem. Soc., 1957, 79, vol 13, 3455-3456; Winston Ho et al, Alkylglycidic Acids; Potential New Hypoglycemic Agents, J. Med. Chem., 1986, 29, 2184-2190; and Hari Babu Mereyala et al, Simple Entry into Isonucleosides: Synthesis of 6-amino-9-[(3S,4S,5R)-4-hydroxy-5-(hydroxymethyl)tetrahydrofuran-3-yl]purine, Tetrahedron Letters, 45 (2004), 295-2966.

It is an object of the present invention to provide a process for the preparation of cyclic ethers from dihydroxy compounds or polyols.

According to the present invention, a process of preparing cyclic ethers comprises reacting under substantially anhydrous conditions at least one organic compound having at least one pair of hydroxyl groups separated by 4 or 5 carbon atoms with an organic carbonate in the presence of a strong base for a period sufficient to effect reaction of said compound to form a cyclic ether, wherein at least one of the hydroxyl groups of said at least one pair of hydroxyl groups is not a tertiary hydroxyl group and said at least one pair of hydroxyl groups is capable of being converted into an ether linkage under the reaction conditions.

Preferably, the hydroxyl groups of said at least one pair of hydroxyl groups are separated by 4 carbon atoms.

The hydroxyl groups of said at least one pair of hydroxyl groups may be primary and primary hydroxyl groups, primary and secondary hydroxyl groups, primary and tertiary hydroxyl groups, secondary and secondary hydroxyl groups and secondary and tertiary hydroxyl groups.

The specific configuration of each hydroxyl group of said at least one pair of hydroxyl groups will depend upon the organic compound under consideration. In one preferred embodiment of the invention, the organic compound is selected such that one of said hydroxyl groups of said at least one pair of hydroxyl groups is a tertiary hydroxyl group. In another preferred embodiment of the invention, the organic compound is selected such that said hydroxyl groups of said at least one pair of hydroxyl groups are primary and secondary hydroxyl groups.

In general, it is particularly preferred that the organic compound is selected such that the hydroxyl groups of said at least one pair of hydroxyl groups are primary and secondary hydroxyl groups, primary and tertiary hydroxyl groups or secondary and tertiary hydroxyl groups.

In one embodiment of the present invention, said organic compound is selected such that it contains only one such pair of hydroxyl groups which is capable of being converted into an ether linkage.

In another embodiment of the present invention, said organic compound is selected such that it contains more than one such pair of hydroxyl groups, preferably two such pairs of hydroxyl groups, each of which is capable of being converted into an ether linkage.

Said organic compound may be a linear or branched, saturated or unsaturated aliphatic compound, a saturated or unsaturated cycloaliphatic compound or an aromatic compound. When branched, the degree of branching and size of the branches should be such that steric hindrance does not pose any problem for the formation of the thermodynamically-stable cyclic ether. Such compounds may also be substituted with other groups provided such groups are groups that will not significantly adversely compete with the desired conversion of the hydroxyl groups of said at least one pair of hydroxyl groups into ether linkages. Such compounds may also contain ether linkages as in alkoxy groups.

Said organic compound may additionally or alternatively be exemplified by Formula 1 below:

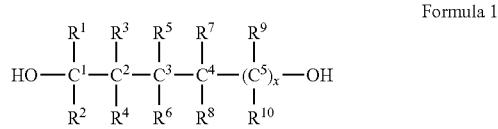

Formula 1 wherein:
the 4 or 5 carbon atoms separating the hydroxyl groups of a pair of hydroxyl groups are labelled $C^1$ to $C^5$;
x=0 or 1, preferably 0;
$R^1$, $R^2$, $R^9$ and $R^{10}$ or, when x=0, $R^1$, $R^2$, $R^7$ and $R^8$ are independently hydrogen, hydroxy alkyl, aliphatic, cycloaliphatic or aromatic groups or may be combined to form cycloaliphatic or aromatic groups;
$R^3$ to $R^8$ or, when x=0, $R^3$ to $R^6$ are independently hydrogen, hydroxy, hydroxyalkyl, aliphatic, cycloaliphatic or aromatic groups or may be combined to form cycloaliphatic or aromatic groups or may be combined to form a second carbon-to-carbon bond between two of said labelled carbon atoms;
provided that:
when x=1, at least one of $R^1$, $R^2$, $R^9$ and $R^{10}$ or when x=0, at least one of $R^1$, $R^2$, $R^7$ and $R^8$ is hydrogen, ie not both hydroxy groups are tertiary;
the bond between $C^2$ and $C^3$ or, if present, between $C^3$ and $C^4$, is a single bond or a cis double bond; and
when at least a second pair of hydroxyl groups is present, the 4 or 5 carbon atoms separating the hydroxyl groups of said second or further pair of hydroxyl groups are located wholly within $R^3$ to $R^8$, or, when x=0, $R^3$ to $R^6$ or, optionally, may include one or two of said carbon atoms labelled $C^1$ to $C^5$ or, when x=0, $C^1$ to $C^4$.

Preferably, said organic compound may additionally or alternatively be exemplified by Formula 1A below:

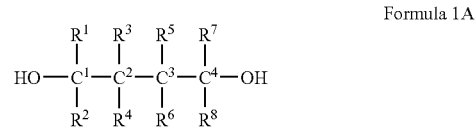

Formula 1A wherein $R^1$ to $R^8$ are as previously defined.

In particular, in Formula 1 or Formula 1A, $R^1$ to $R^{10}$ and $R^1$ to $R^8$, respectively, may include hydroxy alkyl groups such as —$CH_2OH$, —$CH_2CH_2OH$, —$CHOHCH_2OH$ and linear and/or branched alkoxy groups.

In Formula 1 or Formula 1A, if $R^1$ to $R^{10}$ and $R^1$ to $R^8$, respectively, are substituted with other groups, such other groups are groups that will not significantly adversely compete with the desired cyclisation reaction occurring on the hydroxyl groups of said at least one pair of hydroxyl groups.

In one preferred embodiment of the invention, $R^1$, $R^2$ and $R^3$ are hydrogen. More preferably, $R^4$ is hydrogen or a hydroxyl group or, together with $R^5$ or $R^6$, is a carbon-carbon bond.

In one preferred embodiment of the invention, said organic compound has one pair of hydroxyl groups and is selected from the group consisting of aliphatic diols, cycloaliphatic diols and hydroxyalkyl phenols.

Examples of typical aliphatic diols are butane-1,4-diol, 2-butene-1,4-diol, pentane-1,4-diol and pentane-1,5-diol.

Preferably, when the organic compound is a cycloaliphatic compound, the compound is an alkyl-substituted cycloaliphatic compound and one of the hydroxy groups of said pair is attached to said alkyl chain and the other of the hydroxy groups of said pair is attached directly to the cycloaliphatic ring structure. Preferably, said alkyl chain is attached to a ring carbon atom adjacent to the ring carbon atom to which the hydroxy group is directly attached. An example of such a dihydroxy compound is 8α,12-dihydroxy-13,14,15,16-tetranorlabdane, the structure of which is shown above.

In one preferred embodiment of the invention, the cycloaliphatic diol is 8α,12-dihydroxy-13,14,15,16-tetranorlabdane and the cyclic ether formed is (−)-norlabdane oxide.

An example of a hydroxy alkyl phenol as specified above is 2-(2-hydroxyethyl)-phenol.

In another preferred embodiment of the invention, said organic compound is selected from the group consisting of pentitols and hexitols, more especially hexitols. The pentitols may be xylitol, adonitol and arabitol. Preferably, the hexitols are selected from sorbitol, mannitol and iditol; more especially the hexitol is sorbitol.

In another preferred embodiment of the invention, the organic compound has two pairs of hydroxyl groups and is a hexitol and the cyclic ether formed is a diether, ie isosorbide, isomannide or isoidide, preferably isosorbide.

Preferably, the organic carbonate is selected from the group consisting of Formula 2:

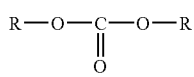

Formula 2 wherein each R is independently aryl or linear or branched, saturated or unsaturated alkyl, alkoxyalkyl or allyl group.

More preferably, the organic carbonate is a dialkyl carbonate, the alkyl groups of which may be the same or different and may be cyclic. Preferably, the alkyl groups are selected from $C_1$ to $C_{18}$ alkyl groups, more preferably from $C_1$ to $C_{10}$ alkyl groups, more particularly $C_1$ to $C_6$ alkyl groups and especially $C_1$ to $C_4$ alkyl groups. Examples of such dialkyl carbonates include dimethyl carbonate, ethyl methyl carbonate, diethyl carbonate, propyl methyl carbonate, isopropyl methyl carbonate, isopropyl ethyl carbonate, butyl methyl carbonate, secondary-butyl methyl carbonate, isobutyl methyl carbonate, tertiary-butyl methyl carbonate, cyclohexyl methyl carbonate, dipropyl carbonate, dibutyl carbonate and diallyl carbonate. Preferred dialkyl carbonates are dimethyl and diethyl carbonate.

When the organic carbonate is a cyclic aliphatic carbonate, preferably the cyclic aliphatic chain derived may be $C_2$ or $C_3$ alkyl groups. Examples of such cyclic aliphatic carbonates are ethylene carbonate and 1,2-propylene carbonate.

Preferably, the organic carbonate is present in a molar ratio of organic carbonate to organic compound of at least 0.9:1, more especially of at least 1:1 with respect to the or each pair of hydroxyl groups of said organic compound; or expressed differently, to each hydroxyl pair capable of being converted into an ether linkage. It will be appreciated that, in relation to compounds such as sorbitol when it is desired to make a diether, the molar ratio of organic carbonate to organic compound of at least 0.9:1, more especially of at least 1:1 for each hydroxyl pair capable of being converted into an ether linkage means that the overall molar ratio will be at least 1.8:1, more especially 2:1.

In some embodiments of the invention, the molar ratio of organic carbonate to organic compound is not more than about 1.5:1 for each hydroxyl pair capable of being converted into an ether linkage.

In other embodiments of the invention, the molar ratio of organic carbonate to organic compound is at least 1.5:1, more particularly at least 2:1 and is especially at least 2.5:1 for each hydroxyl pair capable of being converted into an ether linkage. In such embodiments, the molar ratio of organic carbonate to organic compound is preferably not more than 25:1, more preferably not more than 15:1, more particularly not more than 10:1 and especially not more than 5:1 for each hydroxyl pair capable of being converted into an ether linkage. In such embodiments, the particularly preferred molar ratios of organic carbonate to organic compound are in the range 2:1 to 10:1, more particularly in the range 2.5:1 to 10:1, and especially in the range 2.5:1 to 5:1 for each hydroxyl pair capable of being converted into an ether linkage.

Water will cause decomposition of the organic carbonate; consequently, the reaction is performed under anhydrous conditions.

Preferably, the base is selected from the group consisting of alkoxy, carbonate and hydroxide bases or mixtures thereof. More preferably, the base is an alkali metal alkoxide, carbonate or hydroxide. The alkali metal alkoxides may be methoxides, ethoxides or butoxides. Preferred bases are selected from the group consisting of sodium methoxide, potassium tert-butoxide, cesium carbonate and potassium carbonate.

Another useful class of bases is tetraalkyl ammonium alkoxides, carbonates or hydroxides, more particularly hydroxides. Particularly useful tetraalkyl ammonium bases are those attached to a solid substrate.

The base may be present in an amount of at least 1 mol % up to about 400 mol % relative to the amount of said organic compound. Preferably, the base is present in catalytic quantities. Preferably, the base is present in at least 1 mol %, more preferably at least 5 mol %, more particularly at least 10 mol %, and especially at least 15 mol % relative to the amount of said organic compound. Preferably, the base is present in not more than 100 mol %, more especially not more than 60 mole % relative to the amount of said organic compound. It is particularly preferred that the base is present in an amount of about 20 mol % to about 60 mol % relative to the amount of the said organic compound, ie the molar ratio of base to said organic compound is about 0.2:1 to about 0.6:1

In one embodiment of the invention, the reaction is performed under reflux conditions. The temperature at which the reaction is carried out is dependent upon the reactants and whether any solvent is present which affects the reflux temperature. Typically, reflux temperatures at atmospheric pressure in the range of about 50° C., more preferably about 70° C., and more especially about 80° C., to about 200° C. are used to carry out the reaction.

In another embodiment of the invention, the reaction is carried out in a sealed autoclave in which an autogenous pressure is generated in dependence on the temperature at which the reaction is carried out. Preferably, the temperature at which the reaction is carried out is at least 70° C., more preferable at least 90° C., and more especially at least 100° C. Preferably, the temperature at which the reaction is carried out is not more than 200° C., more especially not more than 180° C. Typically, such reaction temperatures generate autogenous pressures in the region of 0.5 bar to about 40 bar.

In both such embodiments, it is preferred that the reaction temperature is maintained substantially constant throughout the reaction period.

A solvent may be used as part of the reaction mixture to facilitate the physical mixing of the system. Solvents such as hydrocarbon solvents and alcohols may be used. Typically the solvent may be alcohol, preferably the alcohol related to the carbonate being used, for example methanol with dimethyl carbonate. Other alcohols eg ethanol, allyl alcohol, polyether alcohols could be used to effect the relative reflux temperatures. Another solvent which may be used is tetrahydrofuran.

The invention will now be described further with reference to the following Examples.

EXAMPLE 1

8α,12-dihydroxy-13,14,15,16-tetranorlabdane (1 g, 3.93 mmol) and dimethyl carbonate (5 ml, 55.4 mmol) were placed in a three-necked flask equipped with a magnetic stirrer, nitrogen gas inlet, a condenser and gas outlet. The reaction mixture was heated to a reflux temperature of 90° C., ie the reflux temperature of the dimethyl carbonate, following which the base potassium t-butoxide (0.9 g, 7.86 mmol) was added to the reaction mixture. At the end of the addition, the mixture was further refluxed for three hours. The reaction mixture was then cooled to room temperature and filtered to remove inorganic salts. The solid residue was washed with diethyl ether (ca. 10 ml). The filtrate was then concentrated under reduced pressure to recover the (−)-norlabdane oxide as pure white crystals in 91% yield (0.85 g). The (−)-norlabdane oxide product was identified using NMR.

EXAMPLE 2

Example 1 was repeated but varying the amounts of the base (Samples 1 to 3), the amount of dimethyl carbonate ("DMC") (Sample 4) and the type of base used (Sample 5). The reactants, reaction conditions and results are given in Table 1 below.

EXAMPLE 3

Synthesis of
2-methyl-2-(1,3,3-trimethylbutyl)tetrahydrofuran 4,5,7,7-tetramethyl-1,4-octadiol (8.0 g, 39.5 mmol), potassium t-butoxide (8.9 g, 79.3 mmol) and t-butanol solvent (50 mls) were placed in a 100 ml round-bottomed flask, equipped with a condenser and a thermometer. The reaction mixture was heated to reflux (~80 deg C.) and stirred for two hours. The solution turned slightly yellow but no reaction took place. After cooling, from reflux, dimethyl carbonate (10.6 g, 117.7 mmol) was added dropwise to this mixture over a period of 20 minutes. A precipitate formed instantly and stirring became difficult. A further 20 ml of t-butanol was added to facilitate stirring. The mixture was heated at reflux for one hour and left to cool (the reaction was complete after ~20 minutes). The reaction was allowed to stand overnight at room temperature. The mixture was quenched with 300 ml of water and the aqueous layer was extracted three times with 100 ml of toluene. The united organic layers were washed three times with water (50 ml) and once with brine (100 ml). The solution was dried with $MgSO_4$ and filtered. The solvent and excess dimethyl carbonate were evaporated off under reduced pressure to yield 9.7 g of crude product which following distillation via a Kugelrohr apparatus (110-165° C./40 mbar) yielded 5.6 g (30.4 mmol, 77% yield) of isolated product.

EXAMPLE 4

8α,12-dihydroxy-13,14,15,16-tetranorlabdane, dimethyl carbonate and the selected base were introduced into an autoclave equipped with a magnetic stirrer, nitrogen gas inlet and gas outlet. The reaction mixture was heated to the chosen temperature. The reaction mixture was then cooled to room temperature and filtered to remove inorganic salts. The solid residue was washed with diethyl ether (ca. 10 ml). The filtrate was then concentrated under reduced pressure to recover the (−)-norlabdane oxide as pure white crystals. The (−)-norlabdane oxide product was identified using NMR.

This reaction was repeated using different conditions and/or different bases. The reactants, reaction conditions and results are given in Table 2 below.

EXAMPLE 5

Mixtures of diols, dimethyl carbonate and the selected base were refluxed in an oil bath under nitrogen atmosphere as reported in Tables 3 and 4. Cooled samples of the reaction mixtures were filtered on silica pads and the recovered clear solutions were analysed by gas chromatography.

EXAMPLE 6

Mixtures of anhydrous sorbitol, dimethyl carbonate ("DMC") and selected base were refluxed in an oil bath under nitrogen atmosphere until the reaction showed completion as monitored by HPLC. The reflux condenser was then replaced by a downward distillation set-up with vacuum assembly and the residual dimethyl carbonate and the methanol formed were distilled off at atmospheric pressure. A vacuum was then applied (5 mbar) and the oil temperature was increased to 200° C. to collect distilled isosorbide. The molar quantities used and results are set out in Table 5 below.

EXAMPLE 7

Mixtures of anhydrous sorbitol, ethylene carbonate ("EC") and potassium carbonate were stirred under nitrogen atmosphere in an oil bath maintained at 130° C. until HPLC analysis showed no more changes. The reflux condenser was then replaced by a downward distillation set-up with vacuum assembly. A vacuum was then applied (5 mbar) and the oil bath temperature was increased to 200° C. for distillation of residual ethylene carbonate and ethylene glycol produced followed by isosorbide. The molar quantities used and results are set out in Table 6 below.

EXAMPLE 8

In the quantities shown in Table 7 below, anhydrous sorbitol and potassium carbonate were added to dimethyl carbonate in a stainless steel autoclave equipped with a magnetic stirrer, nitrogen gas inlet and gas outlet. Nitrogen was used to flush air from the autoclave. The autoclave was then heated at the chosen temperature by an electric oven whist operating the magnet stirrer over the period indicated. The reaction temperature was controlled by a thermocouple dipped into the reaction mixture. After cooling down the autoclave, the gaseous components were removed through the side valve. The reaction products were analysed by gas chromatography. The obtained mixture was then purified by column chromatography using dichloromethane/methanol 9/1 as elution mixture. The results are given in the Table 7.

TABLE 1

| | Raw Materials | | | | | Product Pattern by NMR | | Yield |
| | Diol | Base | DMC | Reaction Conditions | | | | (−)-norlabdane oxide isolated |
| | g (Molar Ratio) | g (Molar Ratio) | g (Molar Ratio) | Temperature ° C. | Time Hours | Diol | (−)-norlabdane oxide | Carbonate Derivative** | yield % (g) |
|---|---|---|---|---|---|---|---|---|---|
| 1 | 1 (1) | KOtBut 1.8 (4) | 30 (85) | 90 | 2 | — | 100 | | 81 (0.75) |
| 2 | 1 (1) | KOtBut 0.45 (1) | 30 (85) | 90 | 6 | — | 66 | 33 | — |
| 3* | 1 (1) | KOtBut 0.22 (0.5) | 30 (85) | 90 | 6 | — | — | Mostly | — |

TABLE 1-continued

| | Raw Materials | | | Reaction Conditions | | Product Pattern by NMR | | Yield (−)-norlabdane oxide isolated |
|---|---|---|---|---|---|---|---|---|
| | Diol g (Molar Ratio) | Base g (Molar Ratio) | DMC g (Molar Ratio) | Temperature °C. | Time Hours | (−)-norlabdane Diol oxide | Carbonate Derivative** | yield % (g) |
| 4 | 1 (1) | KOtBut 0.9 (2) | 5 (14) | 90 | 3 | — 100 | — | 91 (0.85) |
| 5 | 1 (1) | NaOMe 1.8 (4) | 10 (28) | 90 | 3 | — 100 | — | 83 (0.76) |

*Comparative
**Carbonate derivative has the formula:

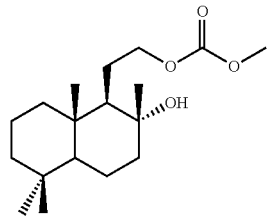

TABLE 2

| | Raw Materials | | | Reaction Conditions | | | Product Pattern by GC | | |
|---|---|---|---|---|---|---|---|---|---|
| | Diol g (Molar Ratio) | Base g (Molar Ratio) | DMC g (Molar Ratio) | Temperature °C. | Time Hours | Pressure Bar | (−)-norlabdane oxide % | Carbonate % | Other Compounds % |
| 6 | 9 (1) | K$_2$CO$_3$ 0.244 (0.05) | 32 (10) | 160 | 20 | 4 | 68 | — | 28 |
| 7 | 9 (1) | K$_2$CO$_3$ 0.244 (0.05) | 32 (10) | 140 | 24 | 2.5 | 63 | — | 36 |
| 8 | 9 (1) | K$_2$CO$_3$ 0.97 (0.2) | 32 (10) | 140 | 6 | 1.5 | 75 | 5 | 18 |
| 9 | 9 (1) | KOtBut 0.198 (0.05) | 32 (10) | 140 | 23 | 2.5 | 83 | — | 14 |
| 10 | 9 (1) | KOtBut 0.8 (0.2) | 32 (10) | 140 | 5 | 1.5 | 100 | — | — |
| 11 | 9 (1) | NaOMe 0.38 (0.2) | 32 (10) | 140 | 4 | 1.5 | 97 | — | — |
| 12 | 9 (1) | NaOMe 0.38 (0.2) | 16 (5) | 160 | 6 | 3 | 88 | — | — |
| 13 | 9 (1) | NaOMe 0.38 (0.2) | 10 (3) | 160 | 6 | 3 | 63 | — | 35 |

TABLE 3

| | Raw Materials | | | Reaction Conditions | | Product Pattern by GC | | |
|---|---|---|---|---|---|---|---|---|
| | Diol g (Molar Ratio) | Base g (Molar Ratio) | DMC g (Molar Ratio) | Temperature °C. | Time Hours | Dihydroxy Compound % | Cyclic Ether % | Other Compounds % |
| 14* | 2-butene-1,4-diol 2 (1) | NaOMe 2.45 (2) | 8 (4) | 85 | 7 | 36 | 64 | — |
| 15* | 2-butene-1,4-diol 2 (1) | NaOMe 0.024 (0.02) | 8 (4) | 85 | 7 | 81 | 13 | 6 |
| 16 | 2-butene-1,4-diol 1 (1) | NaOMe 0.012 (0.02) | 4 (4) | 90 | 7 | 4 | 33 | 61 |
| 17 | 2-butene-1,4-diol 2 (1) | NaOMe 0.025 (0.02) | 8 (4) | 90 | 2 | — | 100 | — |
| 18* | Butane-1,4-diol 2 (1) | NaOMe 2.4 (2) | 8 (4) | 85 | 6 | 35 | 5 | 59 |
| 19* | Pentane-1,5-diol 2 (1) | NaOMe 2 (2) | 3.4 (4) | 85 | 6 | 87 | 3 | 9 |
| 20* | Pentane-1,4-diol 1 (1) | NaOMe 1 (2) | 3.4 (4) | 85 | 7 | 41 | 12 | 40 |

TABLE 3-continued

| | Raw Materials | | | Reaction Conditions | | Product Pattern by GC | | |
|---|---|---|---|---|---|---|---|---|
| | Diol | Base | DMC | Temperature | Time | Dihydroxy | Cyclic | Other |
| | g (Molar Ratio) | g (Molar Ratio) | g (Molar Ratio) | ° C. | Hours | Compound % | Ether % | Compounds % |
| 21 | Pentane-1,5-diol 1 (1) | NaOMe 0.01 (0.02) | 3.4 (4) | 90 | 7 | 12 | 8.5 | 79 |
| 22 | Pentane-1,4-diol 1 (1) | NaOMe 0.01 (0.02) | 3.4 (4) | 90 | 7 | 31 | 29 | 38 |
| 23* | 2-(2-hydroxyethyl)-phenol 0.5 (1) | NaOMe 0.43 (2) | 8 (4) | 85 | 5 | 31 | 33 | 35 |
| 24* | 2-(2-hydroxyethyl)-phenol 0.5 (1) | NaOMe 0.43 (2) | 1.5 (4) | 85 | 5 | 30 | 35 | 30 |
| 25* | 2-(2-hydroxyethyl)-phenol 0.5 (1) | NaOMe 0.01 (0.05) | 1.5 (4) | 85 | 5 | 54 | 22 | 30 |
| 26 | 2-(2-hydroxyethyl)-phenol 1 (1) | NaOMe 0.08 (0.02) | 1.5 (4) | 90 | 2 | 8 | 92 | — |
| 27 | 2-(2-hydroxyethyl)-phenol 0.5 (1) | KOtBut 0.81 (2) | 10 (30) | 90 | 0.5 | — | 100 | — |

*Reaction mixture included 30 g of MeOH.
All percentages calculated by GS-MS data.

TABLE 4

Comparative

| | Raw Materials | | | Reaction Conditions | | Product Pattern by GC | | |
|---|---|---|---|---|---|---|---|---|
| | Diol | Base | DMC | Temperature | Time | Dihydroxy | Cyclic | Other |
| | g (Molar Ratio) | g (Molar Ratio) | g (Molar Ratio) | ° C. | Hours | Compound % | Ether % | Compounds % |
| 28 | 2,5-dimethyl-hexane-2,5-diol 1 (1) | NaOMe 0.07 (0.02) | 2.46 (4) | 90 | 6 | 100 | — | — |

All percentages calculated by GS-MS data.

TABLE 5

| | Raw Materials | | | Reaction Conditions | | Product Isosorbide |
|---|---|---|---|---|---|---|
| | Diol | Base | DMC | Temperature | Time | yield % - |
| | g (Molar Ratio) | g (Molar Ratio) | g (Molar Ratio) | ° C. | Hours | isolated |
| 29 | 50 (1) | $K_2CO_3$ 0.76 (0.02) | 99 (4) | 100 | 24 | 73 |
| 30 | 70 (1) | $K_2CO_3$ 1.07 (0.02) | 86.6 (2.5) | 100 | 24 | 61 |
| 31** | 20 (1) | ZnO 0.45 (0.05) | 29.7 (3) | 100 | 24 | 0 |

**Comparative

TABLE 6

| | Raw Materials | | | Reaction Conditions | | Product Isosorbide |
|---|---|---|---|---|---|---|
| | Diol | Base | EC | Temperature | Time | yield % - |
| | g (Molar Ratio) | g (Molar Ratio) | g (Molar Ratio) | ° C. | Hours | isolated |
| 32 | 75 (1) | $K_2CO_3$ 1.15 (0.02) | 79.8 (2.2) | 110 | 24 | 63 |
| 33 | 75 (1) | $K_2CO_3$ 1.15 (0.02) | 79.8 (2.2) | 130 | 24 | 51 |

TABLE 7

| | Raw Materials | | | Reaction Conditions | | | Product Isosorbide |
|---|---|---|---|---|---|---|---|
| | Diol g (Molar Ratio) | Base g (Molar Ratio) | DMC g (Molar Ratio) | Temp. °C. | Time Hours | Pressure Bar | yield % - isolated |
| 34 | 10 (1) | K$_2$CO$_3$ 0.38 (0.05) | 20 (4) | 180 | 6 | 35 | 50 |
| 35 | 10 (1) | K$_2$CO$_3$ 0.38 (0.05) | 20 (4) | 160 | 6 | 28 | 53 |
| 36 | 10 (1) | K$_2$CO$_3$ 0.38 (0.05) | 20 (4) | 140 | 6 | 20 | 53 |

What is claimed is:

1. A process of preparing (−)-norlabdane oxide comprising: reacting 8α,12-dihydroxy-13,14,15,16-tetranorlabdane with an organic carbonate in the presence of a strong base for a period sufficient to effect reaction of said 8α,12-dihydroxy-13,14,15,16-tetranorlabdane to form (−)-norlabdane oxide.

2. A process of preparing a cyclic ether, the method comprising: reacting at least one organic compound selected from the group consisting of sorbitol, mannitol and iditol with an organic carbonate in the presence of a strong base for a period sufficient to effect reaction of said organic compound to form a cyclic diether; wherein the cyclic ether formed is a diether.

3. A process according to claim 2 wherein said organic compound is sorbitol, and the cyclic ether formed is isosorbide.

4. A process according to claim 1 wherein the organic carbonate is selected from the group consisting of dimethyl carbonate and diethyl carbonate.

5. A process according to claim 1 wherein the organic carbonate is present in at a molar ratio of organic carbonate to organic compound of at least 0.9:1 with respect to each pair of hydroxyl groups of said organic compound capable of being converted into an ether linkage.

6. A process according to claim 1 wherein the organic carbonate is present in a molar ratio of organic carbonate to organic compound of not more than 25:1 with respect to each pair of hydroxyl groups of said organic compound capable of being converted into an ether linkage.

7. A process according to claim 1 wherein the base is selected from the group consisting of alkoxy, carbonate and hydroxide bases or mixtures thereof.

8. A process according to claim 1 wherein the base is an alkali metal or a tetraalkyl ammonium base.

9. A process according to claim 1 wherein the base is present in an amount of at least 1 mol % up to about 400 mol % relative to the amount of said organic compound.

10. A process according to claim 1 wherein the base is present in an amount of about 20 mol % to about 60 mol % relative to the amount of said organic compound.

11. A process according to claim 1 wherein the reaction mixture is heated to a temperature within the range of 50° C. to 200° C.

12. A process according to claim 1 wherein the temperature to which the reaction mixture is heated is maintained substantially constant throughout the reaction period.

13. A process according to claim 1 wherein the reaction occurs in a sealed reaction vessel.

* * * * *